United States Patent
Yu et al.

(10) Patent No.: US 12,410,188 B2
(45) Date of Patent: Sep. 9, 2025

(54) ADENOSINE RECEPTOR ANTAGONIST

(71) Applicant: XIAMEN BIOTIME BIOTECHNOLOGY CO., LTD., Xiamen (CN)

(72) Inventors: Zhiyong Yu, Hangzhou (CN); Shifeng Liu, Hangzhou (CN); Yongqiang Shi, Hangzhou (CN)

(73) Assignee: XIAMEN BIOTIME BIOTECHNOLOGY CO., LTD., Xiamen (CN)

( * ) Notice: Subject to any disclaimer, the term of this patent is extended or adjusted under 35 U.S.C. 154(b) by 878 days.

(21) Appl. No.: 17/630,846

(22) PCT Filed: Jul. 29, 2020

(86) PCT No.: PCT/CN2020/105428
§ 371 (c)(1),
(2) Date: Jan. 27, 2022

(87) PCT Pub. No.: WO2021/018172
PCT Pub. Date: Feb. 4, 2021

(65) Prior Publication Data
US 2022/0267350 A1    Aug. 25, 2022

(30) Foreign Application Priority Data
Jul. 30, 2019 (CN) .......................... 201910696954.3

(51) Int. Cl.
C07D 498/04    (2006.01)
(52) U.S. Cl.
CPC .................................. *C07D 498/04* (2013.01)
(58) Field of Classification Search
None
See application file for complete search history.

(56) References Cited

U.S. PATENT DOCUMENTS

| | | | |
|---|---|---|---|
| 5,356,894 A | 10/1994 | Rodney et al. | |
| 2010/0041676 A1 | 2/2010 | Hirst et al. | |
| 2012/0059162 A1 | 3/2012 | Kusakabe et al. | |
| 2014/0142113 A1 | 5/2014 | Burnet et al. | |
| 2015/0210690 A1 | 7/2015 | Fleury et al. | |
| 2016/0145383 A1 | 5/2016 | Ito et al. | |
| 2020/0048270 A1 | 2/2020 | Wang et al. | |
| 2021/0032253 A1 | 2/2021 | Lu et al. | |

FOREIGN PATENT DOCUMENTS

| | | |
|---|---|---|
| CN | 102532137 | 7/2012 |
| CN | 105985354 A | 10/2016 |
| CN | 105992763 A | 10/2016 |
| JP | WO 2015005206 | 3/2017 |
| WO | WO0011003 A1 | 3/2000 |
| WO | WO 2000/059907 | 10/2000 |
| WO | WO 2001/092264 | 12/2001 |
| WO | WO 2002/055083 | 7/2002 |
| WO | WO 2003/048165 | 6/2003 |
| WO | WO 2004/009443 | 1/2004 |
| WO | WO 2004/110454 | 12/2004 |
| WO | WO2005037843 A1 | 4/2005 |
| WO | WO 2005/040155 | 5/2005 |
| WO | WO 2011/005871 | 1/2011 |
| WO | WO2011013729 A1 | 2/2011 |
| WO | WO 2011/095625 | 8/2011 |
| WO | WO 2012/076974 | 6/2012 |
| WO | WO 2016/135048 | 9/2016 |
| WO | WO 2016/150901 | 9/2016 |
| WO | WO 2016/164838 | 10/2016 |
| WO | WO 2018/161910 | 9/2018 |
| WO | WO 2018/178338 | 10/2018 |
| WO | WO 2019/154294 | 8/2019 |

OTHER PUBLICATIONS

CAS RN 1843231-58-2 (entered into STN on Jan. 9, 2016) (Year: 2016).*
Wamhoff et al., "Efficient Synthesis of Fused Isothiazole C-Nucleosides, 2. Synthesis of 8-Aza-7,9-deaza-7-thiaguanosine and 8-Aza-7,9-deaza-7-thiaadenosine", J.Org. Chem. 29:1912-1917, 1994.
Jiang et al., "Discovery of potential nicotinic acid receptor agonists from Chinese herbal medicines based on molecular simulation", China Academic Journal Electronic Publishing House vol. 39, Issue 23, Dec. 2014.
Office Communication issued in corresponding Japanese Application No. 2022-506115 dated Dec. 5, 2022 {English translation}.
English translation of International Search Report issued in International Application No. PCT/CN2020/105429, dated Nov. 3, 2020.

* cited by examiner

*Primary Examiner* — Craig D Ricci
(74) *Attorney, Agent, or Firm* — pH IP Law

(57) ABSTRACT

A compound represented by formula (I) and a pharmaceutical composition thereof. The compound represented by formula (I) can be used as an adenosine receptor inhibitor, in particular, A2A and/or A2B inhibitors, for example, can be used for preventing or treating diseases related to A2A and/or A2B activity or expression level.

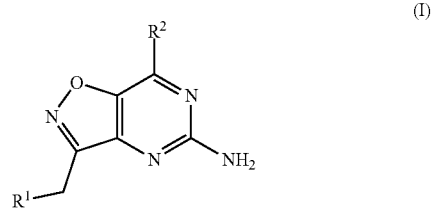

4 Claims, No Drawings

ADENOSINE RECEPTOR ANTAGONIST

This application is a national phase application under 35 U.S.C. § 371 of International Application No. PCT/CN2020/105428, titled "ADENOSINE RECEPTOR ANTAGONIST", filed on Jul. 29, 2020, which claims the benefit of priority to Chinese Patent Application No. 201910696954.3, titled "ADENOSINE RECEPTOR ANTAGONIST", filed on Jul. 30, 2019 with the China National Intellectual Property Administration, which is incorporated herein by reference in entirety.

TECHNICAL FIELD

The present invention provides a novel class of heterocyclic compounds, preparation methods therefor and uses thereof as adenosine receptor (particularly A2A and/or A2B receptor) antagonists.

BACKGROUND ART

Some breakthrough progress has been made on checkpoint inhibitors in the field of immunotherapy. A large number of clinical studies have demonstrated that PD-1/PDL-1 antibodies have certain clinical effects on a variety of tumors (small cell lung cancer, melanoma, head and neck cancer, renal cancer, etc.), but the response rate of single-agent is generally low, ranging from 20% to 40%. Solid tumors include not only tumor cell components, but also a considerable number of other non-tumor cell components found in tumor tissues, which constitute the so-called tumor microenvironment and play an important role in tumor invasion, proliferation, and metastasis. Studies have shown that the combination of PD-1/PDL-1 antibodies and other immunomodulatory small molecules (eliminating the immune tolerance of tumor microenvironment) is one of the effective means to solve the low response rate.

Normally, a human body may effectively control tumor cells by relying on a complete immune mechanism, and T lymphocytes, NK cells, and macrophages have killing effects on the tumor cells, however, when the functions of the cancer cells or the immune cells are changed, the cancer cells can escape from the immune system of the body, forming tumors by malignant hyperplasia. As a signaling molecule used in vivo to limit inflammation and immune responses, adenosine will be greatly elevated in metabolic disorders and cell injury. Activated adenosine receptors are involved in the immune regulation of the body, maintaining higher levels in many different types of tumor microenvironments. The adenosine produced by tumors may interact with adenosine receptors (ARs) on the surface of invading immune cells; there are four subtypes of ARs, described as A1, A2A, A2B, and A3, belonging to a group of G protein-coupled receptors (GPCR) and mainly coupling to Gs and Ga proteins. Each receptor shows a different affinity for adenosine, wherein A1R, A2AR and A3R are high-affinity receptors that may be activated by adenosine at a lower concentration (250-700 nM); while A2BR is a low-affinity receptor which requires higher concentrations (25 µM) of adenosine for activation. Adenosine receptors may also be classified according to the induction of downstream signal small molecule cAMP, when A2A and A2B receptors are activated, a conformational change in the receptor results in the release of activated Cis proteins, activation adenylyl cyclase, and acceleration of the conversion of ATP to cAMP. The increased production of cAMP often accompanied by strong immunosuppression is inhibited by activation of A1 and A3 receptors, thus the activation is generally considered to activate immunization.

Adenosine A2A receptors are predominantly localized in the striatum of the brain, the spleen, the thymus, lymphocytes, and platelets, also found to be localized in the heart, lung, and blood vessels, frequently expressed in cells of the immune system such as T cells. NK cells, macrophages, and dendritic cells. Early use of A2A receptor antagonists was primarily used for the treatment of nervous system diseases in the early stage, such as Parkinson's disease, Huntington's disease. Alzheimer's disease, attention-deficit related disorders, and psychosis, in recent studies, A2A receptor antagonists have been found to improve the antigen presentation of dendritic cells, the activation and killing ability of T cells and natural killer cells, inhibit regulatory T cells (T-regs), MDSCs and TAM, eliminate tumor immune tolerance, and promote the occurrence of an anti-tumor immune response, leading to tumor regression. Therefore, A2A receptor antagonists may be one of the effective methods for the treatment of tumors. A2A receptor antagonists may be used alone or in combination with other anti-tumor drugs, especially in combination with immune checkpoint inhibitors, which is a hotspot in clinical research.

Adenosine A2B receptors are expressed in a variety of tissues, vasculature, the brain, small intestine, and tumors, and also in a variety of cells, including mast cells, dendritic cells, neutrophils, macrophages, and lymphocytes in the immune system, as well as endothelial cells, neural cells, and glial cells. The wide expression of the A2B receptor makes it a target for the study of a variety of diseases, including cardiovascular diseases, pulmonary diseases, diabetes, and cancer. Studies have shown that A2B antagonists can prevent the growth of tumors (bladder cancer, breast cancer), and high expression of A2B in patients with triple-negative breast cancer can also lead to a reduced survival rate in the treatment.

International Patent Application Publication Nos. WO2018/178338, WO2011/095625, WO2001/92264, WO2003/048165, WO2004/09443, WO2002/055083, etc. disclose compounds useful as A2A receptor antagonists, and international Patent Application Publication WO2005/040155, WO2016/164838, WO2016/150901, WO20161/35048, WO2015/05206, WO2012/076974, WO2011/005871, and Chinese Patent Application Publication No. CN102532137, and U.S. Patent Application Publication No. Us 20140142113, etc. disclose compounds useful as A2B receptor antagonists. However, there is still a need for inhibitors having a better inhibitory effect on adenosine receptors; in particular, the antagonists capable of inhibiting both A2A and A2B receptors have important clinical value and therapeutic significance, but few reports are available. There is an urgent need in the art for adenosine inhibitors with better inhibitory effects, in particular novel antagonist compounds capable of simultaneously inhibiting A2A and A2B receptors.

SUMMARY OF THE INVENTION

After long and intensive studies, we have unexpectedly found a class of heterocyclic compounds with good A2A and/or A2B receptor inhibitory activity.

Based on the above findings, in a first aspect of the present invention, there is provided a compound of Formula (I), or a pharmaceutically acceptable salt, a prodrug, an isotopic derivative, a hydrate, an isomer, a solvate, or a metabolite thereof.

Formula (I)

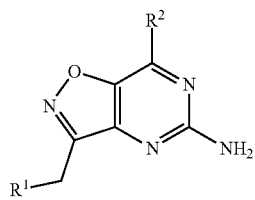

wherein:
R¹ and R² each independently represent: $C_3$-$C_{12}$ cycloalkyl, 3-12 membered heterocycloalkyl, $C_6$-$C_{12}$ aryl, 5-12 membered heteroaryl;

wherein the R¹ and R² are optionally each independently substituted with 0, 1, 2, 3, 4, or 5 substituents selected from R³, wherein R³ is selected from the group consisting of $C_1$-$C_6$ alkyl, hydroxy ($C_1$-$C_6$ alkyl)-, $C_2$-$C_6$ alkenyl, $C_2$-$C_6$ alkynyl, $C_3$-$C_6$ cycloalkyl, $C_6$-$C_{12}$ aryl, 5-12 membered heteroaryl, $C_1$-$C_6$ haloalkyl, halogen, oxo, nitro, cyano, —NR$^a$R$^b$, —OR$^a$, —SR$^a$, —SOR$^a$, —SO$_2$R$^a$, —SO$_3$R$^a$, —NR$^a$(O)R$^a$, —NR$^a$(O)OR$^a$, —NR$^a$S(O)$_2$R$^a$, —C(O)OR$^a$, —C(O)NR$^a$R$^b$, —C(O)R$^a$, —(CR$^a$R$^b$)$_m$—OR$^a$, —(CR$^a$R$^b$)$_m$—NR$^a$R$^b$, —(CR$^a$R$^b$)$_m$—NR$^a$—(CR$^a$R$^b$)$_n$—OR$^a$, —(CR$^a$R$^b$)$_m$—O—(CR$^a$R$^b$)$_n$—NR$^a$R$^b$, —(CR$^a$R$^b$)$_m$—O—(CR$^a$R$^b$)$_n$—OR$^a$ and —(CR$^a$R$^b$)$_m$—NR$^a$—(CR$^a$R$^b$)$_n$—NR$^a$R$^b$; or when the number of substituents is 2, and the 2 substituents are located in adjacent positions, they are optionally cyclized with each other into saturated or unsaturated 4- to 7-membered rings, and further, the ring optionally contains 0, 1 or 2 heteroatoms selected from O, S, or N;

R$^a$ and R$^b$ each independently represent hydrogen, halogen, $C_1$-$C_6$ alkyl, $C_3$-$C_6$ cycloalkyl, —($C_6$-$C_6$ alkylene)-($C_6$-$C_{12}$)aryl;

alternatively, when being attached to the same atom, R$^a$ and R$^b$ together with the atom bound thereto are optionally cyclized to each other into 3- to 7-membered rings optionally containing 0, 1, or 2 heteroatoms selected from O, N, or S;

n and m each independently represent 0, 1, 2, 3, or 4.

Preferably, the compound of Formula (I) has the following structure of Formula (II):

Formula (II)

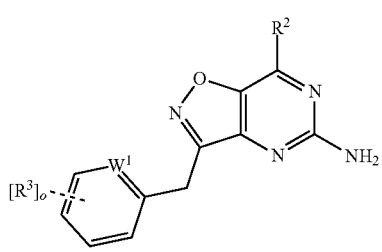

wherein W₁ is selected from CR⁴ or N, and R⁴ has the same definition as R¹, R² and R³ are as defined for Formula (I), and o is 0, 1, 2, or 3.

Preferably, the compound of Formula (I) has the following structure of Formula (III):

Formula (III)

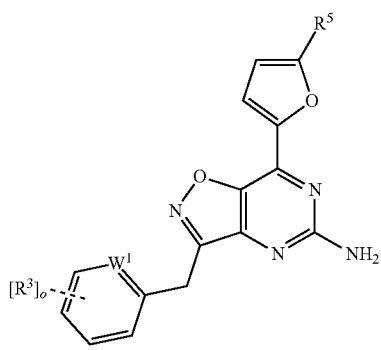

wherein R⁵ is selected from hydrogen, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_1$-$C_6$ alkoxy, $C_1$-$C_6$ alkylthio, halogen, nitro, —NR$^c$R$^d$, cyano, —SO$_2$R$^c$, —SO$_3$R$^c$; is selected from CR⁴ or N, R⁴ has the same definition as R³; R³ is as defined in claim 1, and o is 0, 1, 2, or 3.

where R$^c$ and R$^d$ each independently represent hydrogen, halogen, $C_1$-$C_6$ alkyl, or $C_3$-$C_6$ cycloalkyl.

alternatively, when being attached to the same atom, R$^c$ and R$^d$ together with the atom bound thereto are optionally cyclized to each other into 3- to 7-membered rings optionally containing 0, 1, or 2 heteroatoms selected from O, N, or S.

Preferably, the compound of the present invention is selected from the following structures:

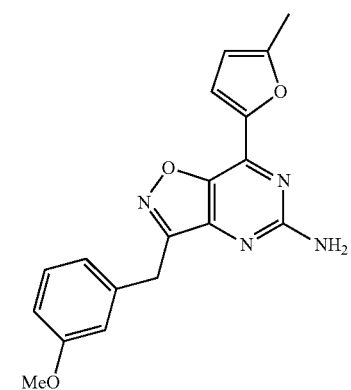

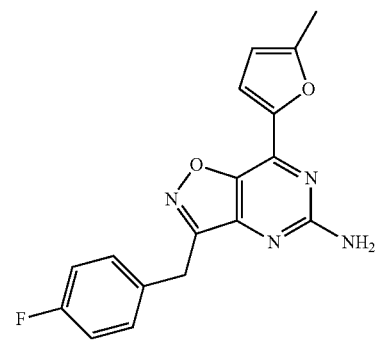

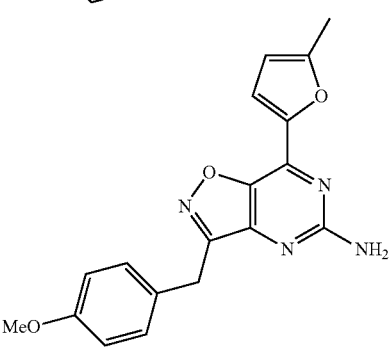

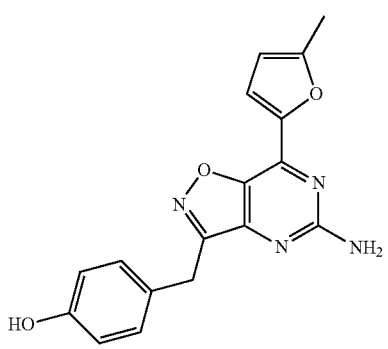

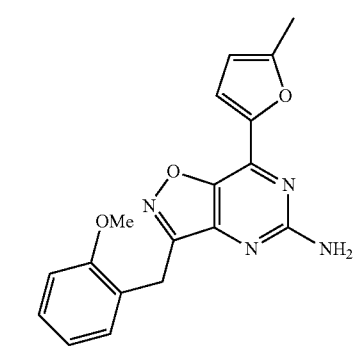

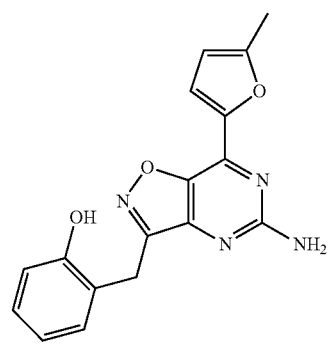

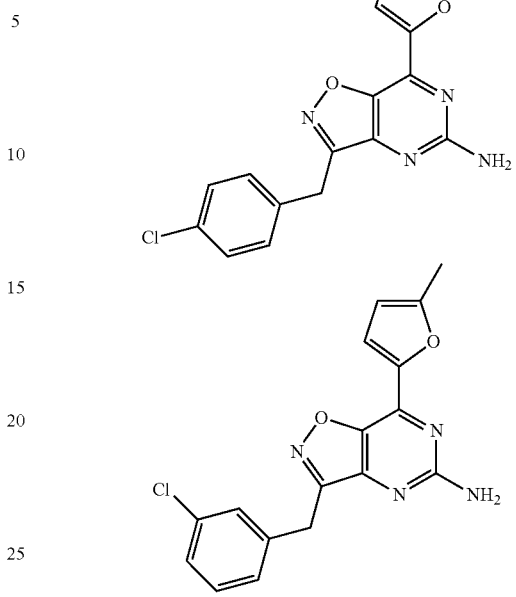

The compounds of the present invention may also be prepared in the form of pharmaceutically acceptable salts which may be formed with inorganic or organic acids such as hydrochloric acid, hydrobromic acid, sulfuric acid, phosphoric acid, nitric acid, acetic acid, glycolic acid, lactic acid, pyruvic acid, malonic acid, succinic acid, glutaric acid, fumaric acid, malic acid, mandelic acid, tartaric acid, citric acid, ascorbic acid, palmitic acid, maleic acid, hydroxymaleic acid, benzoic acid, hydroxybenzoic acid, phenylacetic acid, cinnamic acid, salicylic acid, methanesulfonic acid, benzenesulfonic acid or toluenesulfonic acid.

The pharmaceutically acceptable salts of the present invention may be prepared by a conventional method, for example, by dissolving the compound of the present invention in a water-miscible organic solvent (e.g., acetone, methanol, ethanol, and acetonitrile), adding an excess of an aqueous organic or inorganic acid thereto to precipitate the salt from the resulting mixture, removing the solvent and remaining free acid therefrom, and then isolating the precipitated salt.

The compounds of the present invention (or including pharmaceutically acceptable salts thereof) may include solvate for us thereof, preferably, the solvates are hydrates.

The present invention also provides use of the compound of the present invention in the manufacture of a medicament for the prevention and treatment of a disease which may be regulated by the inhibition of the activity of an adenosine receptor. Preferably, the disease is selected from the group consisting of cancer, tumors, inflammatory diseases, autoimmune diseases, and immune-mediated diseases.

Furthermore, the present invention provides a pharmaceutical composition for the prevention or treatment of cancer, tumors, inflammatory diseases, autoimmune diseases, neurodegenerative diseases, attention-related diseases, or immune-mediated diseases, including the compound Formula (I) of the present invention as an active ingredient.

Furthermore, the present invention provides a method of inhibiting an adenosine receptor comprising exposing the adenosine receptor to a compound of the present invention. Preferably, the present invention provides a method of inhibiting the A2A and/or A2B receptor comprising exposing the A2A and/or A2B receptor to a compound of the present invention. Furthermore, the present invention provides a method for the prevention or treatment of cancer, tumors, inflammatory diseases, autoimmune diseases, neurodegenerative diseases, attention-related diseases, or immune-mediated diseases, including administering to a mammal in need thereof a compound of the present invention.

Representative examples of cancers or tumors may include, but are not limited to, skin cancer, bladder cancer, ovarian cancer, breast cancer, gastric cancer, pancreatic cancer, prostate cancer, colon cancer, lung cancer, bone cancer, brain cancer, neurocytoma, rectal cancer, colon cancer, familial adenomatous polyposis cancer, hereditary nonpolyposis colorectal cancer, esophageal cancer, lip cancer, laryngeal cancer, hypopharyngeal cancer, tongue cancer, salivary gland cancer, gastric cancer, adenocarcinoma, medullary thyroid cancer, papillary thyroid cancer, renal cancer, carcinoma of renal parenchyma, ovarian cancer, cervical cancer, corpus carcinoma, endometrial cancer, choriocarcinoma, pancreatic cancer, prostate cancer, testicular cancer, carcinoma of urinary system, melanoma, brain tumors such as glioblastoma, astrocytoma, meningioma, medulloblastoma and peripheral neuroectodermal tumors, Hodgkin's lymphoma, non-Hodgkin's lymphoma, Burkitt's lymphoma, acute lymphoblastic leukemia (ALL), chronic lymphocytic leukemia (CLL), acute myelogenous leukemia (AML), chronic myelogenous leukemia (CML), adult T-cell leukemia lymphoma, diffuse large B-cell lymphoma (DLBCL), hepatocellular carcinoma, gallbladder carcinoma, bronchial carcinoma, small cell lung carcinoma, non-small cell lung carcinoma, multiple myeloma, basal cell tumor, teratoma, retinoblastoma, choroidal melanoma, seminoma, rhabdomyosarcoma, craniopharyngioma, osteosarcoma, chondrosarcoma, myosarcoma, liposarcoma, fibrosarcoma, Ewing's sarcoma, or plasmacytoma.

When a compound of the present invention or a pharmaceutically acceptable salt thereof is administered in combination with another anticancer agent or a checkpoint inhibitor for the treatment of cancer or tumors, the compound of the present invention or a pharmaceutically acceptable salt thereof may provide an enhanced anticancer effect.

Representative examples of anticancer agent for the treatment of a cancer or tumor may include, but are not limited to, cell signal transduction inhibitors, Chlorambucil, Melphalan, Cyclophosphamide, Ifosfamide, Busulfan, Carmustine, Lomustine, Streptozotocin, Cisplatin, Carboplatin, Oxaliplatin, Dacarbazine, Temozolomide, Procarbazine, Methotrexate, Fluorouracil, Cytarabine, Gemcitabine, Mercaptopurine, Fludarabine, Vinblastine, Vincristine, Vinorelbine, Paclitaxel, Docetaxel, Topotecan, Irinotecan, Etoposide, Trabectedin, Dactinomycin, Doxorubicin, Epirubicin, Daunorubicin, Mitoxantrone, Bleomycin, Mitomycin C, Ixabepilone, Tamoxifen, Flutamide, Gonadorelin Analogs, Megestrol, Prednisone, Dexamethasone, Methylprednisolone, Thalidomide, Interferon α, Calcium Folinate, Sirolimus, Sirolimus Lipide, Everolimus, Afatinib, Alisertib, Amuvatinib, Apatinib, Axitinib, Bortezomib, Bosutinib, Brivanib, Cabozantinib, Cediranib, Crenolanib, Crizotinib, Dabrafenib, Dacomitinib, Danusertib, Dasatinib, Dovitinib, Erlotinib, Foretinib, Ganetespib, Gefitinib, Ibrutinib, Icotinib, Imatinib, Iniparib, Lapatinib, Lenvatinib, Linifanib, Linsitinib, Masitinib, Momelotinib, Motesanib, Neratinib Nilotinib, Niraparib, Oprozomib, Olaparib, Pazopanib, Pictiliisib, Ponatinib, Quizartinib, Regorafenib, Rigosertib, Rucaparib, Ruxolitinib, Saracatinib, Saridegib, Sorafenib, Sunitinib, Telatinib, Tivantinib, Tivozanib, Tofacitinib, Trametinib, Vandetanib, Veliparib, Vemurafenib, Erivedge, Volasertib, Alemtuzumab, Bevacizumab, Brentuximab Vedotin, Catumaxomab, Cetuximab, Denosumab, Gemtuzumab, Ipilimumab, Nimotuzumab, Ofatumumab, Panitumumab, Rituximab, Tositumomab, and Trastuzumab; the checkpoint inhibitor includes but not limited to anti-PD-1 antibodies, anti-PD-L1 antibodies, LAG3 antibodies. TIM-3 antibodies, and anti-CTLA-4 antibodies, or any combination thereof.

Representative examples of inflammatory diseases, autoimmune diseases, and immune-mediated diseases may include, but are not limited to, arthritis, rheumatoid arthritis, spondyloarthritis, gouty arthritis, osteoarthritis, juvenile arthritis, other arthritic conditions, lupus, systemic lupus erythematosus (SLE), skin-related diseases, psoriasis, eczema, dermatitis, allergic dermatitis, pain, lung disease, lung Inflammation, adult respiratory distress syndrome (ARDS), pulmonary sarcoidosis, chronic pulmonary inflammatory disease, chronic obstructive pulmonary disease (COPD), cardiovascular disease, atherosclerosis, myocardial infarction, congestive heart failure, myocardial ischemia-reperfusion injury, inflammatory bowel disease, Crohn's disease, ulcerative colitis, irritable bowel syndrome, asthma, Sjogren's syndrome, autoimmune thyroid disease, urticaria (rubella), multiple sclerosis, scleroderma, organ transplant rejection, xenotransplantation, idiopathic thrombocytopenic purpura (ITP), Parkinson's disease, Alzheimer's disease, diabetes-related diseases, inflammation, pelvic inflammatory diseases, allergic rhinitis, allergic bronchitis, allergic sinusitis, leukemia, lymphoma, B-cell lymphoma, T-cell lymphoma, myeloma, acute lymphocytic leukemia (ALL), chronic lymphocytic leukemia (CLL), acute myelogenous leukemia (AML), chronic myelogenous leukemia (CML), hairy cell leukemia, Hodgkin's disease, non-Hodgkin's lymphoma, multiple myeloma, myelodysplastic syndrome (MDS), myeloproliferative tumor (MPN), diffuse large B-cell lymphoma, and follicular lymphoma. When a compound of the present invention or a pharmaceutically acceptable salt thereof is administered in combination with another therapeutic agent for the treatment of inflammatory diseases, autoimmune diseases and immune-mediated diseases, the compound of the present invention or a pharmaceutically acceptable salt thereof may provide an enhanced therapeutic effect.

Representative examples of therapeutic agents for the treatment of inflammatory diseases, autoimmune diseases, and immune-mediated diseases may include, but are not limited to, steroidal drugs (e.g., prednisone, prednisolone, methylprednisolone, cortisone, hydroxycortisone, betamethasone, dexamethasone, etc.), methotrexate, leflunomide, anti-TNF α agents (e.g., etanercept, infliximab, adalimumab, etc.), calcineurin inhibitors (e.g., tacrolimus, pimecrolimus, etc.), and antihistamines (e.g., diphenhydramine, hydroxyzine, loratadine, ebastine, ketotifen, cetirizine, levocetirizine, fexofenadine, etc.), and at least one therapeutic agent selected therefrom may be included in the pharmaceutical compositions of the present invention.

The compound of the present invention or a pharmaceutically acceptable salt thereof can be administered orally or parenterally as an active ingredient in an effective amount ranging from 0.1 mg/kg body weight/day to 2,000 mg/kg body weight/day, preferably 1 mg/kg, body weight/day to 1,000 mg/kg body weight/day in the case of mammals including humans (body weight about 70 kg), and administered in a single or four divided doses per day, or following/not following a predetermined time. The dosage of the active ingredient may be adjusted according to several relevant factors, such as the condition of the subject to be treated, the type and severity of the disease, the rate of administration, and the opinion of the physician). In some cases, amounts less than the above doses may be suitable. If it does not cause harmful side effects, an amount larger than the above dose can be used and the amount can be administered in divided doses per day.

The pharmaceutical compositions of the present invention may be formulated into dosage forms, such as tablets, granules, powders, capsules, syrups, emulsions, microemulsions, solutions, or suspensions, for oral or parenteral administration chiding intramuscular, intravenous, and subcutaneous routes) according to any of the conventional methods.

The pharmaceutical compositions of the present invention for oral administration may be prepared by mixing the active ingredients with carriers such as cellulose, calcium silicate, corn starch, lactose, sucrose, dextrose, calcium phosphate, stearic acid, magnesium stearate, calcium stearate, gelatin, talc, surfactants, suspending agents, emulsifying agents, and diluents. Examples of carriers employed in the injectable compositions of the present invention consist of water, saline solutions, dextrose solutions, glucose-like solutions, alcohols, glycols, ethers e.g., polyethylene glycol 400), oils, fatty acids, fatty acid esters, glycerides, surfactants, suspending agents, and emulsifying agents.

Additional features of the present invention will become apparent from the description of exemplary embodiments of the present invention which are presented for purposes of illustration and are not intended to be limiting thereof, the following examples being prepared, isolated, and characterized using the methods disclosed herein.

The compounds of the present invention may be prepared in a variety of ways known to those skilled in the art of organic synthesis and may be synthesized using the synthetic methods known in the art of organic synthetic chemistry, or by variations thereof known to those skilled in the art. The required reaction may be carried out in a solvent or solvent mixture suitable for the kit materials used and for the transformations achieved.

DETAILED DESCRIPTION OF THE INVENTION

After long-term and intensive research, the inventors have unexpectedly found a class of heterocyclic compounds as shown in Formula (I) having adenosine receptor inhibitory activity, particularly A2A and/or A2B inhibitory activity. Based on the above findings, the inventors have completed the present invention.

Terms

Terms used in the present application, including the specification and claims, are defined as follows, unless otherwise indicated. It must be noted that, in the description and the appended claims, the nouns without a numerical modification typically include plural referents unless the context clearly dictates otherwise. If not stated otherwise, conventional methods of mass spectrometry, nuclear magnetic, HPLC, protein chemistry, biochemistry, recombinant DNA techniques, and pharmacology are used.

Throughout the specification and claims, a given chemical formula or name shall encompass all stereo and optical isomers and racemates in which such isomers exist. Unless otherwise indicated, all chiral (enantiomer and diastereoisomer) and racemic, forms are within the scope of the present invention. Many geometric isomers of C=C double bonds, C=N double bonds, and ring systems may also be present in the compounds, and all the above-mentioned stable isomers are encompassed in the present invention, Cis- and trans- (or E- and Z-) geometric isomers of the compounds of the present invention are described herein and may be isolated as mixtures of isomers or as separated isomeric forms. The compounds of the present invention may be isolated in optically active or racemic forms. All methods for preparing the compounds of the present invention and intermediates prepared therein are considered part of the present invention. In preparing enantiomeric or diastereomeric products, they can be isolated by conventional methods, for example, by chromatography or fractional crystallization. Depending on the process conditions, the final products of the present invention are obtained in free (neutral) or salt form. Both the free forms and salts of these end products are within the scope of the present invention. If desired, one form of the compound may be converted to another form. The free base or acid may be converted to its salt form; the salt may be converted to the free compound or another salt; mixtures of isomeric compounds of the present invention may be isolated into the individual isomers. The compounds, free forms, and salts thereof of the present invention may exist in a variety of tautomeric forms in which hydrogen atoms are transposed onto other parts of the molecule and the chemical bonds between the atoms of the molecule are thus rearranged. It is to be understood that all tautomeric forms which may exist are included in the present invention.

Unless otherwise defined, when a substituent is labeled "optionally substituted", the substituent is selected from, for example, the following substituents consisting of alkyl, cycloalkyl, aryl, heterocyclyl, halogen, hydroxy, alkoxy, oxo, alkanoyl, aryloxy, alkanoyloxy, amino, alkylamino, arylamino, arylalkylamino, disubstituted amine group (in which two amino substituents are selected from alkyl, aryl or arylalkyl), alkanoylamino, aroylamino, aralkanoylamino, substituted alkanoylamino, substituted arylamino, substituted aralkanoylamino, thio, alkylthio, atylthio, arylalkylthio, arylthiocarbonyl, arylalkylthiocarbonyl, alkylsulfonyl, arylsulfonyl, arylalkylsulfonyl, sulfonamido such as —$SO_2NH_2$, substituted sulfonamido, nitro, cyano, carboxy, carbamoyl such as —$CONH_2$, substituted, carbamoyl such as —CONH alkyl, —CONH aryl, —CONH arylalkyl or the case where there are two substituents selected from alkyl, aryl or arylalkyl on the nitrogen, alkoxycarbonyl, aryl, substituted aryl, guanidine, heterocyclyl such as indolyl, imidazolyl, furanyl, thienyl, thiazolyl, pyrrolidinyl, pyridyl, pyrimidinyl, pyrrolidinyl, piperidinyl, morpholinyl, piperazinyl and homopiperazinyl, and substituted heterocyclyl.

As used herein, the term "alkyl" or "alkylene" is intended to include both branched- and straight-chain saturated aliphatic hydrocarbon groups having the specified number of carbon atoms. For example, "$C_1$-$C_6$ alkyl" denotes an alkyl group having 1 to 6 carbon atoms. Examples of alkyl groups include, but are not limited to, methyl (Me), ethyl (Et), propyl (e.g., n-propyl and isopropyl), butyl (e.g., n-butyl, isobutyl, tert-butyl), and pentyl (e.g., n-pentyl, isopentyl, neopentyl). Preferred alkyl groups are $C_1$-$C_6$ alkyl groups, and more preferred alkyl groups are $C_1$-$C_4$ alkyl groups.

The term "alkenyl" denotes a straight or branched chain hydrocarbon group containing one or more double bonds and typically 2 to 20 carbon atoms in length. For example, "$C_2$-$C_6$ alkenyl" contains 2 to 8 carbon atoms. Alkenyl groups include, but are not limited to, for example, ethenyl, propenyl, butenyl, 1-methyl-2-buten-1-yl, heptenyl, and octenyl. Preferred alkenyl groups are $C_2$-$C_8$ alkenyl groups, and more preferred alkenyl groups are $C_2$-$C_6$ alkenyl groups.

The term "alkynyl" denotes a straight or branched chain hydrocarbon group containing one or more triple bonds and typically 2 to 20 carbon atoms in length. For example, "$C_2$-$C_8$ alkynyl" contains 2 to 8 carbon atoms. Preferred alkenyl groups are $C_2$-$C_6$ alkynyl groups, and more preferred alkenyl groups are $C_2$-$C_6$ alkynyl groups. Representative alkynyl groups include, but are not limited to, for example, ethynyl, 1-propynyl, 1-butynyl, heptynyl, and octynyl.

The term "alkoxy" or "alkyloxy" refers to —O-alkyl. "$C_1$-$C_6$ alkoxy" (or alkyloxy) is intended to include $C_1$, $C_2$, $C_3$, $C_4$, $C_5$, and $C_6$ alkoxy groups. Preferred alkoxy groups are $C_1$-$C_6$ alkoxy groups, more preferred alkoxy groups are $C_1$-$C_4$ alkoxy groups. Examples of alkoxy groups include, but are not limited to, methoxy, ethoxy, propoxy (e.g., n-propoxy and isopropoxy), and t-butoxy. Similarly, "alkylthio" or "thioalkoxy" means an alkyl group, as defined above, with the specified number of carbon atoms linked via a sulfur bridge; for example, methyl-S— and ethyl-S—.

The term "carbonyl" refers to an organic functional group (C=O) composed of two carbon and oxygen atoms linked by a double bond.

The term "aryl", alone or as part of a larger moiety such as "aralkyl", "aralkoxy", or "aryloxyalkyl", refers to a monocyclic, bicyclic, or tricyclic ring system having a total of 5 to 12 ring members, where at least one ring in the system is aromatic and where each ring in the system contains 3 to 7 ring members. Monocyclic aromatic refers to phenyl, bicyclic or polycyclic aromatic group refers to naphthyl, anthryl, etc., meanwhile, the aryl bicyclic, ring may be formed by fusing a cycloalkyl group, or a cycloalkenyl group or a cycloalkynyl group on a benzene ring. Preferred aryl groups are $C_6$-$C_{17}$ aryl groups. In certain embodiments of the present invention, "aryl" refers to an aromatic ring system including, but not limited to, phenyl, biphenyl, indanyl, 1-naphthyl, 2-naphthyl, and tetrahydronaphthyl. The term "aralkyl" or "arylalkyl" refers to an alkyl residue attached to an aryl ring. Non-limiting examples include benzyl, and phenethyl. The fused aryl group may be attached to another group at a suitable position on the cycloalkyl ring or the aromatic ring. For example, an arrow line drawn from a ring system indicates that the bond may be attached to any suitable ring atom.

The term "cycloalkyl" refers to a monocyclic or bicyclic alkyl group. Monocyclic alkyl refers to $C_3$-$C_8$ cyclic alkyl including, but not limited to, cyclopropyl, cyclobutyl, cyclopentyl, cyclohexyl, and norbornyl. Branched cycloalkyl such as 1-methylclopropyl and 2-methylclopropyl are included in the definition of "cycloalkyl". Bicyclic alkyl includes bridged, spiro, or fused cycloalkyl. Preferred cycloalkyl groups are $C_3$-$C_6$ cycloalkyl groups.

The term "cycloalkenyl" refers to a monocyclic or bicyclic, alkenyl group. Monocyclic alkenyl refers to $C_3$-$C_8$ cyclic alkenyl including, but not limited to, cyclopropenyl, cyclobutenyl, cyclopentenyl, cyclohexenyl, and norbornenyl. Branched cycloalkenyl such as 1-methylclopropenyl and 2-methylclopropenyl are included in the definition of "cycloalkenyl". Bicyclic alkenyl includes bridged, spiro or fused cyclic alkenyl.

"Halo" or "halogen" includes fluoro, chloro, bronco, and iodo. "Haloalkyl" is intended to include both branched and straight-chain saturated aliphatic hydrocarbon groups having the specified number of carbon atoms and substituted with one or more halogens. Examples of haloalkyl include, but are not limited to, fluoromethyl, difluoromethyl, trifluoromethyl, trichloromethyl, pentafluoroethyl, pentachloroethyl, 2,2,2-trifluoroethyl, heptafluoropropyl, and heptachloropropyl. Examples of haloalkyl also include "fluoroalkyl" groups intended to include branched- and straight-chain saturated aliphatic hydrocarbon groups having the specified number of carbon atoms and substituted with one or more fluorine atoms.

"Haloalkoxy" or "haloalkyloxy" denotes a haloalkyl group, as defined above, having the indicated number of carbon atoms linked via an oxygen bridge. For example, "$C_1$-$C_6$ haloalkoxy" is intended to include $C_1$, $C_2$, $C_3$, $C_4$, $C_5$, and $C_6$ haloalkoxy groups. Examples of haloalkoxy include, but are not limited to, trifluoromethoxy, 2,2,2-trifluoroethoxy, and pentafluoroethoxy. Similarly, "haloalkylthio" or "thiohaloalkoxy" denotes a haloalkyl group, as defined above, having the indicated number of carbon atoms linked via a sulfur bridge; for example, trifluoromethyl-S— and pentafluoroethyl-S—.

The term "heteroaryl" means a stable 3-, 4-, 5-, 6-, or 7-membered aromatic monocyclic or aromatic bicyclic or 7-, 8-, 9-, 10-, 11-, 12-, 13-, or 14-membered aromatic polycyclic heterocycle, which is fully unsaturated, partially unsaturated, and contains carbon atoms and 1, 2, 3 or 4 heteroatoms independently selected from N, O and S; and includes any polycyclic group in which any heterocycle defined above is fused to a benzene ring. The nitrogen and sulfur heteroatoms may optionally be oxidized. The nitrogen atom is substituted or unsubstituted (i.e., N or NR, where R is H or another substituent if defined). The heterocycle may be attached to its pendant group at any heteroatom or carbon atom that results in a stable structure. If the resulting compound is stable, the heterocyclyl groups described herein may be substituted on a carbon or nitrogen atom. The nitrogen in the heterocycle may be optionally quaternized. Preferably, when the total number of S and O atoms in the heterocycle exceeds 1, then these heteroatoms are not adjacent to each other. Preferably, the total number of S and O atoms in the heterocycle is not greater than 1. Preferred heteroaryl groups are 5-12-membered heteroaryl groups. Examples of heteroaryls include, but are not limited to, acridinyl, azetidinyl, azocinyl, benzimidazolyl, benzofuranyl, benzothiofuranyl, benzothienyl, benzoxazolyl, benzoxazolinyl, benzothiazolyl, benzotriazolyl, benzotetrazolyl, benzisoxazolyl, benzisothiazolyl, benzimidazolinyl, carbazotyl, 4aH-carbazolyl, carbolinyl, chromanyl, chromenyl, cinnolinyl, decahydroquinolinyl, 2H, 6H-1,5,2-dithiazinyl, dihydrofuro[2,3-b]tetrahydrofuranyl, furanyl, furazanyl, imidazolidinyl, imidazolinyl, imidazolyl, 1H-indazolyl, imidazopyridinyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isothiazolopyridinyl, isoxazolyl, isoxazolopyridinyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolopyridinyl, oxazolidinyl, perimidinyl, oxindolyl, pyrimidinyl, phenanthridinyl, phenanthrolinyl, phenazinyl, phenothiazinyl, phenoxathiinyl, phenoxazinyl, phthalazinyl, piperazinyl, piperidinyl, piperidonyl, 4-piperidenyl, piperonyl, pteridinyl, purinyl, pyranyl, pyrazinyl, pyrazolidinyl, pyrazolinyl, pyrazolopyridinyl, pyrazolyl, pyridazinyl, pyridooxazolyl, pyridoimidazolyl, pyridothiazolyl, pyridinyl, pyrimidinyl, pyrrolidinyl, pyrrolinyl, 2-pyrrolidonyl, 2H-pyrrolyl, pyrrolyl, quinazolinyl, quinolinyl, 4H-quinolizinyl, quinoxalinyl, quinuclidinyl, tetrazolyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thiazolopyridyl, thienothiazolyl, thienooxazolyl, thienoimidazolyl, thienyl, triazinyl, 1,2,3-triazolyl, 1,2,4-triazolyl, 1,2,5-triazolyl, 1,3,4-triazolyl and xanthenyl, quinolinyl, isoquinolinyl, phthalazinyl, quinazolinyl, indolyl, isoindolyl, indolinyl, 1H-indazolyl, benzimidazoly, 1,2,3,4-tetrahydroquinolinyl, 1,2,3,4-tetrahydroisoquinolinyl, 5,6,7,8-tetrahydro-quinolinyl, 2,3-dihydro-benzofuranyl, chromanyl, 1,2,3,4-tetrahydro-quinoxalinyl and 1,2,3,4-tetrahydro-quinazolinyl. The present invention also includes fused and spiro compounds containing, for example, the above heterocycles.

As used herein, the term "heterocycloalkyl" refers to a monocyclic heterocycloalkyl system or a bicyclic heterocycloalkyl system, and also includes spiroheterocycles or bridged heterocycloalkyl groups. The monocyclic heterocycloalkyl refers to a saturated or unsaturated but not aromatic 3- to 8-membered cyclic alkyl system containing at least one atom selected from O, N, S, and P. The bicyclic heterocycloalkyl system refers to a heterocycloalkyl group fused with a phenyl, or a cycloalkyl, or a cycloalkenyl, or a heterocycloalkyl, or a heteroaryl group. Preferred heterocycloalkyl groups are 3-12-membered heterocycloalkyl groups.

As used herein, the term "substituted" means that at least one hydrogen atom is replaced with a non-hydrogen group, provided that normal valency is maintained and that the substitution results in a stable compound. As used herein, the ring double bond is a double bond (e.g., C=C, C=N, or N=N) formed between two adjacent ring atoms.

In the case where nitrogen atoms (e.g., amities) are present on the compounds of the present invention, these nitrogen atoms may be converted to N-oxides by treatment with an oxidizing agent (e.g., m-CPBA and/or hydrogen peroxide) to obtain other compounds of the present invention. Thus, the nitrogen atoms shown and claimed are considered to encompass both the nitrogen shown and its N-oxides to obtain the derivatives of the present invention.

When any variable occurs more than once in any composition or formula of a compound, its definition at each occurrence is independent of its definition at every other occurrence. Thus, for example, if a group is shown to be substituted with 0, 1, 2, or 3 R groups, the group may be optionally substituted with up to three R groups, and at each occurrence, R is independently selected from the definition of R. Furthermore, combinations of substituents and/or variables are permissible only if such combinations result in stable compounds.

The term "solvate" means a physical association of a compound of the present invention with one or more solvent molecules (whether organic or inorganic). The physical association includes hydrogen bonding. In some cases, for example, when one or more solvent molecules are incorporated in the crystal lattice of the crystalline solid, the solvate will be capable of being isolated. The solvent molecules in the solvate may be present in a regular and/or disordered arrangement. Solvates may include stoichiometric or non-stoichiometric solvent molecules. "Solvate" encompasses both solution-phase and isolatable solvates. Exemplary solvates include, but are not limited to, hydrates, ethanolates, methanolates, and isopropanolates. Methods of solvation are well known in the art.

As used herein, the term "patient" refers to an organism treated by the methods of the present invention. Such organisms preferably include but are not limited to, mammals (e.g., murine, ape/monkey, equine, bovine, swine, canine, feline, etc.) and most preferably refer to humans.

As used herein, the term "effective amount" means an amount of a drug or pharmaceutical age (i.e., a compound of the present invention) that will elicit the biological or medical response of a tissue, system, animal, or human that is being sought, for example, by a researcher or clinician. Furthermore, the term "therapeutically elective amount" means an amount that results in improved treatment, cure, prevention or alleviation of a disease, condition, or side effect, or a reduction in the rate of progression of a disease or condition, as compared to a corresponding subject not receiving such an amount. An effective amount can be administered in one or more dosing, administrations, or dosages and is not intended to be limited by the particular formulation or route of administration. The term also includes an amount effective that enhances normal physiological function within its scope.

As used herein, the term "treating" includes any effect that results in amelioration of a condition, disease, or disorder, for example, alleviation, reduction, modulation, amelioration or elimination, or amelioration of a symptom thereof. As used herein, a compound or pharmaceutical composition, upon administration, may result in amelioration of a disease, symptom, or condition, particularly amelioration of the severity, delay of the onset, alleviation of the progression, or reduction of the duration of the condition. Regardless of fixed administration or temporary administration, continuous administration, or intermittent administration, it may be attributed to or related to the administration. The terms "prevent", "preventing" and "prevention" as used herein refer to preventing, blocking, eliminating the onset of disease, or interfering with or slowing the progression of a disease before the onset of a disease or condition.

The term "pharmaceutical composition" as used herein refers to the combination of an active agent with an inert or active carrier, making the composition particularly suitable for in vivo or ex vivo diagnosis or treatment. Examples of bases include, but are not limited to, alkali metal (e.g., sodium) hydroxides, alkaline earth metal (e.g., magnesium) hydroxides, ammonia, etc. Salts of the compounds of the present invention are expected to be pharmaceutically acceptable for therapeutic use. However, non-pharmaceutically acceptable salts of acids and bases may also be used, for example, in the preparation or purification of pharmaceutically acceptable compounds.

The term "pharmaceutically acceptable" is used herein to refer to those compounds, materials, compositions, and/or dosage forms as follows: within the scope of sound medical judgment, suitable for use in contact with the tissues of humans and animals without undue toxicity, irritation, allergic response, and/or other problems or complications, commensurate with a reasonable benefit/risk ratio.

As used herein, the phrase "pharmaceutically acceptable carrier" or "medicinal carrier" refers to a pharmaceutical material, composition, or a vehicle, such as a liquid or solid filler, diluent, excipient, manufacturing adjuvant (e.g., lubricant, talc, magnesium stearate, calcium stearate or zinc stearate or stearic acid), or solvent encapsulating material, which refers to carrying or transporting the active compound from one organ or portion of the body to another organ or portion of the body. Each carrier must be "acceptable" in the sense of being compatible with the other ingredients of the formulation and not deleterious to the patient.

Specific Pharmaceutical and Medical Terms

The term "acceptable", as used herein, refers to a prescription component or active ingredient that does not unduly adversely affect the health of the general therapeutic target.

The term "cancer", as used herein, refers to uncontrolled abnormal growth of cells and is capable of metastasis (transmission) under certain conditions. This type of cancer includes, but is not limited to, solid tumors (e.g., bladder, bowel, brain, chest, uterus, heart, kidney, lung, lymphoid tissue (lymphoma), ovary, pancreas, or other endocrine organs (e.g., thyroid), prostate, skin (melanoma), or hematological tumors (e.g., aleukemic leukemia).

The term "administered in combination" or similar terms, as used herein, refers to the administration of several selected therapeutic agents to a patient in the same or different modes of administration at the same or different times.

The term "enhance" or "potentiate", as used herein, means that the desired result can be increased or prolonged in potency or duration. Thus, in enhancing the therapeutic effect of a drug, the term "enhance" refers to the ability of the drug to increase or prolong potency or duration in the system. "Synergistic value", as used herein, refers to the ability to maximize the ability of another therapeutic agent in an ideal system.

The term "immunological disease" refers to a disease or condition that responds adversely or deleteriously to endogenous or exogenous antigens. The result is often a dysfunction of the cells, or thus destruction and dysfunction, or destruction of organs or tissues that may produce immune symptoms.

The term "kit" is synonymous with "product package".

The term "subject" or "object" includes mammals and non-mammals. Mammals include, but are not limited to, mammals: human, non-human primates such as chimpanzees, apes and monkeys; agricultural animals such as bovines, equines, goats, sheep, swine; domestic animals such as rabbits, canines; experimental animals include rodents, such as rats, mice, and guinea pigs. Non-mammalian animals include, but are not limited to, birds, and fish. In a preferred embodiment, the selected mammal is a human.

Route of Administration

Suitable routes of administration include but are not limited to, oral, intravenous, rectal, aerosol, parenteral, ophthalmic, pulmonary, transdermal, vaginal, aural, nasal, and topical administration. In addition, by way of example only, parenteral administration includes intramuscular, subcutaneous, intravenous, intramedullary, ventricular, intraperitoneal, intralymphatic, and intranasal injections.

In one aspect, the compounds described herein are administered locally rather than systemically. In particular embodiments, the prolonged action preparation is administered by implantation (e.g., subcutaneously or intramuscularly) or by intramuscular injection. Further, in another embodiment, the drug is administered by a targeted drug delivery system, for example, liposomes encapsulated by organ-specific antibodies. In this particular embodiment, the liposomes are selectively targeted to specific organs and absorbed.

Pharmaceutical Compositions and Dosages

The present invention also provides pharmaceutical compositions including a therapeutically effective amount of one or more compounds of the present invention formulated together with one or more pharmaceutically acceptable carriers (additives) and/or diluents, and optionally one or more of the other therapeutic agents described above. The compounds of the present invention may be administered for any of the above-mentioned uses by any suitable means, for example by orally, such as in the form of tablets, pills, powders, granules, elixirs, tinctures, suspensions (including nanosuspensions, micro suspensions, spray-dried dispersions), syrups and emulsions; by sublingually; by buccally; by parenterally, such as by subcutaneous, intravenous, intramuscular or intrasternal injection or infusion techniques (e.g., in the form of sterile injectable aqueous or nonaqueous solutions or suspensions); by nasally, including administration to the nasal mask, such as by inhalation spray; by topically, such as in the form of a cream or ointment; or by rectally, such as in the form of suppositories. They mar be administered alone, but are generally administered using pharmaceutically acceptable carriers selected based on the chosen route of administration and standard pharmaceutical practice. The pharmaceutically acceptable carriers are formulated according to several factors within the knowledge of those skilled in the art. These factors include but are not limited to: types and properties of the formulated active agents; a subject to be administered the composition containing the active agent; the intended route of administration of the composition; and targeted therapeutic indications. The pharmaceutically acceptable carriers include aqueous and non-aqueous liquid media and various solid and semi-solid dosage forms.

The above-mentioned carrier may include many different ingredients and additives in addition to the active agent, and the above-mentioned other ingredients, for example, stabilizing active agent and binder, are included in the formulation for various reasons known to those skilled in the are. For a description of suitable pharmaceutically acceptable carriers and factors involved in the selection of carrier, see several readily available sources, such as Allen L. V. Jr. et al. Remington: The Science and Practice of Pharmacy (2 Volumes), 22nd Edition (2012), Pharmaceutical Press.

The dosage regimen for the compounds of the present invention will, of course, vary depending upon known factors such as the pharmacodynamic characteristics of the particular agent and its mode and route of administration; species, age, sex, health, medical condition, and weight of the recipient; the nature and extent of symptoms; kind of concurrent treatment; treatment frequency; routes of administration, renal and hepatic function and desired effects in patients. According to general guidelines, when used for a given effect, the daily oral dosage of each active ingredient should be from about 0.001 mg/day to about 10-5000 mg/day, preferably from about 0.01 mg/day to about 1000 mg/day, and most preferably from about 0.1 mg/day to about 250 mg/day. During constant infusion, the most preferred intravenous close should be from about 0.01 mg/kg/min to about 10 mg/kg/min. The compounds of the present invention may be administered in a single daily dose, or the total daily dose may be administered in divided doses of two, three, or four times daily.

The compounds are generally administered in the form of a mixture of suitable pharmaceutical diluents, excipients, or carriers (collectively referred to herein as pharmaceutically acceptable carriers) suitably selected concerning the intended form of administration (e.g., oral tablets, capsules, elixirs, and syrups) and consistent with conventional pharmaceutical practice.

Dosage forms (pharmaceutical compositions) suitable for administration may contain from about 1 mg to about 2000 mg of active ingredient per dosage unit. In these pharmaceutical compositions, the active ingredient will generally be present in an amount of about 0.1-95% by weight, based on a total weight of the composition.

Typical capsules for oral administration contain at least one compound of the present invention (250 mg), lactose (75 mg), and magnesium stearate (15 mg). The mixture was processed through a 60 meshes screen and packaged into No. 1 gelatin capsules.

A typical injectable formulation may be prepared as follows: at least one compound of the present invention (250 mg) was placed in a vial in a sterile manner, and lyophilized and sealed in a sterile manner. For use, the contents in the vial were mixed with 2 mL of normal saline to produce an injectable formulation.

The scope of the present invention includes (alone or in combination with a pharmaceutically acceptable carrier) pharmaceutical compositions containing a therapeutically effective amount of at least one compound of the present invention as an active ingredient. Optionally, the compounds of the present invention may be used alone, in combination with other compounds of the present invention, or in combination with one or more other therapeutic agents (e.g., anticancer agents or other pharmaceutically active agents).

Regardless of the selected route of administration, the compounds of the present invention (which may be used in suitable hydrated forms) and/or the pharmaceutical compositions of the present invention are formulated into pharmaceutically acceptable dosage forms by conventional methods known to those skilled in the art.

The actual dosage level of the active ingredient in the pharmaceutical compositions of the present invention may be varied to obtain an amount of the active ingredient that is effective to achieve the desired therapeutic response, composition, and mode of administration for a particular patient without being toxic to the patient.

The selected dosage level will depend upon a variety of factors, including the factors well known in the medical field such as the activity of the employed specific compound of the present invention, or an ester, salt or amide thereof; routes of administration; administration time; the discharge rate of the employed specific compound; the absorption rate and extent; duration of treatment; other drugs, compounds and/or substances used in combination with the employed specific compounds; the age, sex, weight, condition, general health and prior medical history of the patient being treated.

A physician or veterinarian having ordinary skill in the art can readily determine and prescribe an effective amount of the desired pharmaceutical composition. For example, to achieve the desired therapeutic effect, the physician or veterinarian may start a relatively small amount of the compound of the present invention used in the pharmaceutical composition below the desired level and gradually increase the dosage until the desired effect is achieved. In general, a suitable daily dose of a compound of the present invention will be that amount of the compound that is the lowest dose effective to produce a therapeutic effect. Such an effective dose will generally depend on such factors. In general, oral, intravenous, intracerebroventricular, and subcutaneous doses of a compound of the present invention for a patient range from about 0.01 to about 50 mg/kg body weight/day. If desired, an effective daily dose of the active compound may be administered m two, three, four, five, six, or more sub-doses respectively at appropriate intervals throughout the day, optionally in a unit dosage form. In certain aspects of the present invention, the medication is administered once a day.

Although the compound of the present invention may be administered alone, it is preferably administered in the form of a pharmaceutical preparation (composition).

Kit/Product Package

Kits/product packages are also described herein for the treatment of the above-mentioned indications. These kits may be composed of a conveyor, a medicine pack, or a container box. The container box can be divided into multiple compartments to accommodate one or more containers, such as vials, and test tubes, where each container contains a single component in the method. Suitable containers consist of bottles, vials, syringes, and test tubes. The container is made of an acceptable glass or plastic material.

For example, the container may contain one or more of the compounds described herein; the compound may exist either in the form of a pharmaceutical composition or may exist as a mixture with other ingredients described herein. The container may have a sterile outlet (e.g., the container may be an intravenous infusion bag or bottle and the stopper may be pierced by a hypodermic needle). Such kits may contain a compound and descriptions, labels, or instructions for the method of use described herein.

A typical kit may include one or more containers, each containing one or more materials (e.g., reagents, concentrated stock solutions, and/or equipment) to accommodate commercial promotions and the needs of the user for the use of compounds. Such materials include, but are not limited to, buffers, diluents, filters, needles, syringes, conveyors, bags, containers, bottles, and/or tubes, with a list of contents and/or instructions for use, and with a built-in package. The entire set of instructions must be included.

The label may be displayed on or closely related to the container. The appearance of the label on the container means that the label letters, numbers, or other features are pasted, molded, or engraved on the container; the label can also appear in the container box or shipping box containing a variety of containers, such as in the product insert. A label may be used to indicate a particular therapeutic use of the contents. The label may also indicate directions for the use of contents, such as described in the methods described above.

All of the features described in this specification (including any accompanying claims, abstract, and drawings), and/or all of the steps involved in any method or process, may be present in any combination unless some features or steps are mutually exclusive in the same combination.

The features mentioned above, or the features mentioned in the embodiments mentioned herein, may be combined in any combination. All of the features disclosed in this specification may be combined in any combination, and each feature disclosed in this specification may be replaced by any alternative feature serving the same, equivalent, or similar purpose. Thus, unless otherwise specified, the features disclosed are only general examples of equivalent or similar features.

The present invention will be described in detail below in connection with specific examples. It should be understood that these examples are only used to describe the present ion and are not intended to limit the scope of the present invention. The experimental methods in the following examples which are not specified with specific conditions are generally carried out according to conventional conditions or according to the conditions recommended by the manufacturer. All percentages, ratios, ratios, or parts are calculated by weight unless otherwise stated.

The units in weight-volume percent in the present invention are will known to those skilled in the art and refer, for example, to the weight of solute in a 100 milliliters of solution. Unless otherwise defined, all professional and scientific terms used in the text have the same meaning as those familiar to those skilled in the art. In addition, any methods and materials similar or equivalent to those described can be used in the methods of the present invention. The preferred embodiments and materials described herein are exemplary only.

In preferred embodiments of the present invention, the following compounds are provided, but are not limited to:

The present invention will be described in detail below in connection with specific examples. It should be understood that these examples are only used to describe the present invention and are not intended to limit the scope of the present invention. The experimental methods in the following examples which are not specified with specific conditions are generally carried out according to conventional conditions or according to the conditions recommended by the manufacturer. All percentages and parts are calculated by weight unless otherwise stated.

SPECIFIC EXAMPLES

When no preparative mute is described, related intermediates are commercially available (e.g. from Sigma Aldrich, Alfa).

General Procedure

Commercial reagents were used without further purification. Room temperature refers to 20-27° C. 1 H-NMR spectra were recorded on a Bruker instrument at 500 MHz. Chemical shift values are expressed in parts per million, i.e. δ value. The following abbreviations are used for the multiplicity of NMR signals: s=singlet, brs=broad, d=doublet, t=triplet, m=multiplet. Coupling constants were listed as J values, measured in Hz. NMR and mass spectrum results were corrected for background peaks. Chromatography refers to column chromatography performed using 100 meshes silica gel and completed under nitrogen pressure (flash chromatography). TLC used to monitor the reaction refers to TLC performed using a specific mobile phase and silica gel $F_{254}$ from Merck as stationary phase.

LC-MS Measurements were Performed under the Following Conditions

Instruments: Thermo U3000, ALLtech ELSD, MSQ, UV detector combined ELSD and MSD (flow ratio of 4:1). Column: Waters X-Bridge C-18, 3.5 μm 4.6×50 mm; Column temperature: 30° C. Gradient [Time (min)/solvent B in A (%)]: 0.00/5.0, 0.70/95, 1.40/95, 1.41/5, 1.50/5. (Solvent A=0.01% trifluoroacetic acid in water; solvent B=0.01% trifluoroacetic acid in acetonitrile). UV Detection: 214/254/280/300 nm; DAD detection: 200-400 nm; Flow Rate: 4 mL/min; MS: ESI, 100-1500 m/z.

Preparative HPLC typically used acidic process (gradient of acetonitrile and water, each containing 0.1% formic acid) with a Thermo U3000 AFC-3000; Column: Globalsil C-18 C-18 12 nm, 250×20 mm, 10 μm, or equivalent; Flow Rate: 20 mL/min for separation.

Synthesis of Intermediates

Preparation of Compound INT-1

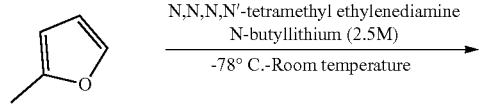

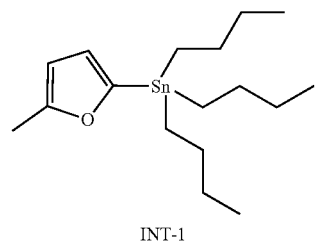

INT-1

2-Methylfuran (3.28 g, 40.0 mmol) and N,N,N',N'-tetramethyl ethylenediamine (17.0 g, 146 mmol) were dissolved in anhydrous tetrahydrofuran (80 mL), N-Butyllithium (2.5 M in n-hexane, 16 mL) was slowly added dropwise under a nitrogen atmosphere at −78° C., the resulting solution was agitated at a temperature ranging from −40° C. to −20° C. for 3 hours, then tributyltin chloride (13.0 g, 40.0 mmol) was added at −78° C., and the resulting solution was slowly heated to room temperature and left standing overnight. The reaction solution was quenched with saturated ammonium chloride (60 mL) and extracted with ethyl acetate (100 mL×3). The combined organic phase was washed with saturated saline solution (100 mL), dried over anhydrous sodium sulfate, and filtered, the filtrate passed through a mixed column of silica gel (100 g) and potassium fluoride (10 g), rinsed with ethyl acetate (300 mL), and the eluent was concentrated under reduced pressure to give the compound INT-1 (12.1 g, yield 81%). $^{1}$H NMR (500 MHz, Chloroform-d) δ 6.44 (d, J=3.0 Hz, 1H), 6.05-5.94 (m, 1H), 2.33 (s, 3H), 1.62-1.48 (m, 6H), 1.37-1.29 (m, 6H), 1.12-0.98 (m, 6H), 0.94-0.87 (m, 9H).

Synthesis of Compounds of Examples

Example 1

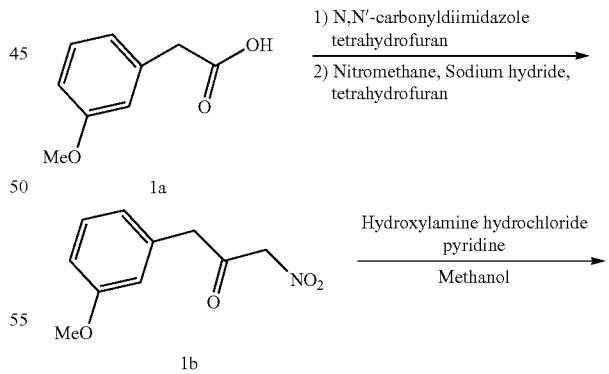

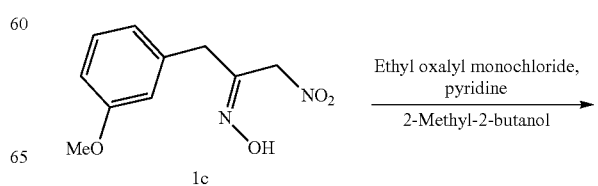

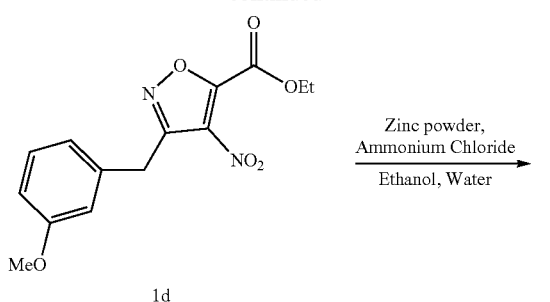

1d

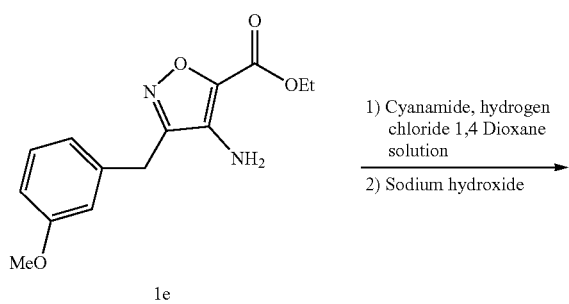

1e

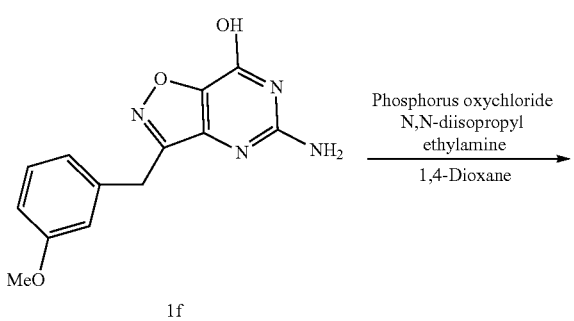

1f

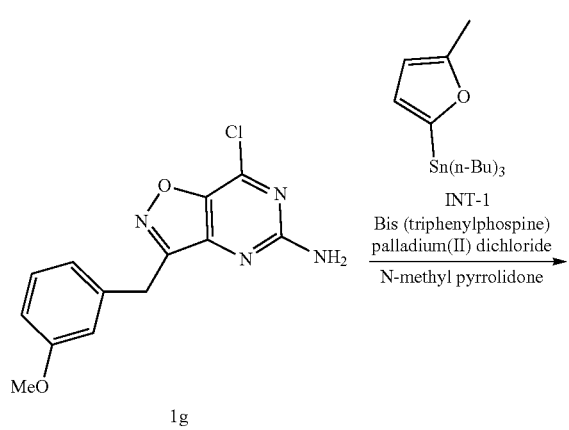

1g

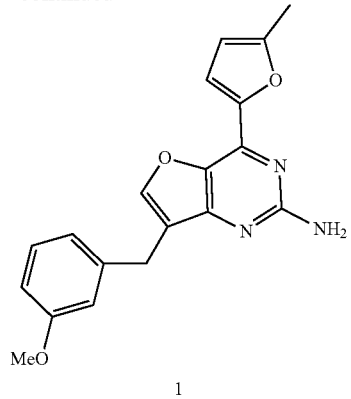

1

To a solution of compound 1a (12.0 g, 72 mmol) in tetrahydrofuran (100 mL) was added N,N'-Carbonyldiimidazole (13.5 g, 83 mmol), and the resulting reaction solution A was agitated for 3 hours at room temperature. Simultaneously, nitromethane (15.6 mL, 289 mmol) was added dropwise to a solution of sodium hydride (purity 60%, dispersed in mineral oil, 3.32 g, 83 mmol) in tetrahydrofuran (100 mL) in an ice bath. The resulting reaction solution B was also agitated for 3 hours in an ice bath. Reaction solution A was then slowly added dropwise to reaction solution B in an ice bath, and the resulting reaction solution was agitated for 18 hours at 50° C. The reaction solution was quenched with hydrochloric acid (1 M, 200 mL) and extracted with ethyl acetate (200 mL×2). The combined organic layer was dried over anhydrous sodium sulfate and filtered, and the filtrate was concentrated to give a crude product, which was purified by column chromatography (dichloromethane/methanol=20/1) to give the compound 1b as a yellow solid (9.0 g, yield: 60%).

To a solution of compound 1b (4.00 g, 19.1 mmol) and pyridine (3.1 mL, 38.2 mmol) in methanol (40 mL) was added hydroxylamine hydrochloride (2.66 g, 38.2 mmol), and the resulting reaction solution was agitated for 2 hours at room temperature. The reaction solution was concentrated to give a crude product, which was purified by column chromatography (petroleum ether/ethyl acetate=1/1) to give the compound 1e as a yellow oil (3.40 g, yield: 79%); the nuclear magnetic resonance showed cis-trans isomers in a ratio of Z/E=2/1.

To a solution of compound 1e (3.40 g, 15.2 mmol) and pyridine (2.44 mL, 30.3 mmol) in 2-methyl-2-butanol (60 mL) was added ethyl oxalyl monochloride (2.55 mL, 22.8 mmol), and the resulting reaction was agitated for 40 hours at room temperature. The reaction solution was concentrated to give a crude product, which was purified by column chromatography (petroleum ether/ethyl acetate=20/1) to give the compound 1d as a yellow oil (1.16 g, yield: 25%). $^1$H NMR (500 MHz, DMSO-d6) δ 7.22 (t, J=7.2 Hz, 1H), 6.82-6.79 (m, 3H), 4.43 (q, J=6.5 Hz, 2H), 4.26 (s, 2H), 3.71 (s, 3H), 1.30 (t, J=6.5 Hz, 3H).

To a solution of compound 1d (1.16 g, 3.8 mmol) in ethanol (15 mL) and water (15 mL) were added zinc powder (2.50 g, 38 mmol) and ammonium chloride (4.10 g, 83 mmol), and the resulting reaction was agitated for 3 hours at room temperature. The reaction solution was filtered, and the filtrate was concentrated and dissolved in a mixed solution of ethyl acetate (50 mL) and water (50 mL). The organic layer phase was dried over anhydrous sodium sulfate and filtered, and the filtrate was concentrated to give the compound 1e (800 mg, yield: 76%). MS: 277.6 [M+H]$^+$.

To a solution of compound 1e (800 mg, 2.9 mmol) in 1,4-dioxane (5 mL) were added cyanamide (487 mg, 11.6 mmol) and hydrochloric acid (4 M in 1,4-dioxane, 5.8 mL), and the resulting reaction solution was agitated for 18 hours at 100° C. The concentrated reaction solution was dissolved in an aqueous solution of sodium hydroxide (2 M, 14.5 mL) and agitated under reflux for 1 hour. The reaction solution was cooled down, then was adjusted to pH=3 with 3 M aqueous hydrochloric acid solution, and the precipitated solid was suction filtered, washed with water (20 mL), and dried to give the compound 1f as a yellow solid (430 mg, yield: 55%), $^1$H NMR (500 MHz, DMSO-d6) δ 11.49 (brs, 1H), 7.19 (t, J=7.5 Hz, 1H), 6.89 (s, 1H), 6.84 (d, J=7.5 Hz, 1H), 6.78 (d, J=7.5 Hz, 1H), 6.62 (brs, 2H), 4.08 (s, 2H), 3.70 (s, 3H); MS: 273.5 [M+H]$^+$.

To a solution of compound 1f (180 mg, 661 μmol) in 1,4-dioxane (3 mL) were added phosphorous oxychloride (811 mg, 5.29 mmol) and N,N-diisopropylethyl amine (342 mg, 2.64 mmol), and the resulting reaction solution was agitated for 8 hours at room temperature. The reaction solution was poured into saturated aqueous sodium bicarbonate (30 mL) and extracted with dichloromethane (30 mL×2). The combined organic phase was dried over anhydrous sodium sulfate and filtered, and the filtrate was concentrated under reduced pressure to give a crude product, which was purified by preparative thin-layer chromatography to give a yellow solid 1 g (50 mg, yield: 26%).

To a solution of compound 1g (50 mg, 172 μmol) in N-methylpyrrolidone (3 mL) were added compound INT-1 (95.8 mg, 258 μmol) and bis (triphenylphosphine) palladium (II) dichloride (24.1 mg, 34.4 μmol), and the resulting solution was left standing for 2 hours at 85° C. The reaction solution was poured into water (30 mL) and extracted with ethyl acetate (30 mL×2). The combined organic layer was dried over anhydrous sodium sulfate, and filtered, and the filtrate was concentrated under reduced pressure to give a crude product, which was purified by column chromatography (petroleum ether/ethyl acetate=1/1) to give the compound 1 (43 mg, yield: 74%). $^1$H NMR (500 MHz, Chloroform d) δ7.63 (s, 1H), 7.23 (t, J=7.5 Hz, 1H), 7.03-7.02 (m, 2H), 6.79 (d, J=7.5 Hz, 1H), 6.36 (s, 1H), 5.55 (brs, 2H), 4.30 (s, 2H), 3.80 (s, 3H), 2.52 (s, 3H); MS: 337.4 [M+H]$^+$.

Example 2

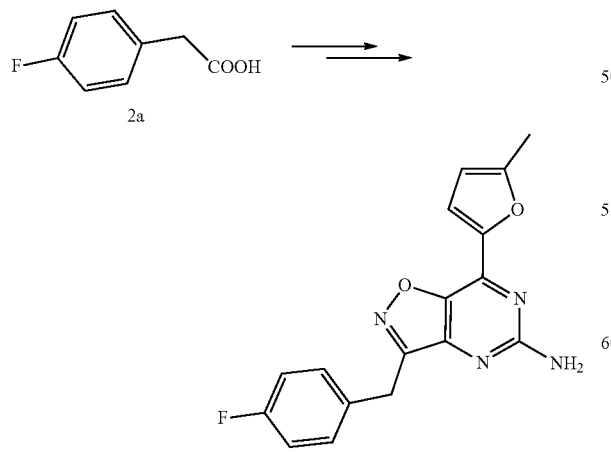

With reference to the preparation method of compound 1, compound 2 may be prepared from compound 2a by the corresponding steps, and the spectral information was as follows: $^1$H NMR (500 MHz, Methanol-d4) δ 7.50 (s, 1H), 7.45-7.39 (m, 2H), 7.07-7.00 (m, 2H), 6.41 (s, 1H), 4.28 (s, 2H), 2.47 (s, 3H); MS: 325.4 [M+H]$^+$.

Example 3

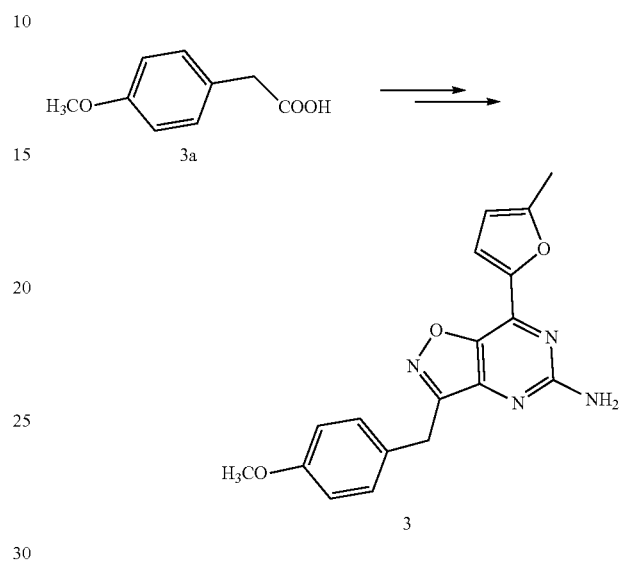

With reference to the preparation method of compound 1, compound 3 may be prepared from compound 3a by the corresponding steps, and the spectral information was as follows: $^1$H NMR (500 MHz, DMSO-d6) δ 7.44 (d, J=3.0 Hz, 1H), 7.28 (d, J=8.5 Hz, 2H), 6.89 (s, 2H), 6.88 (d, J=8.5 Hz, 2H), 6.51 (d, J=3.0 Hz, 1H), 4.20 (s, 2H), 3.72 (s, 3H), 2.45 (s, 3H); MS: 337.5 [M+H]$^+$.

Example 4

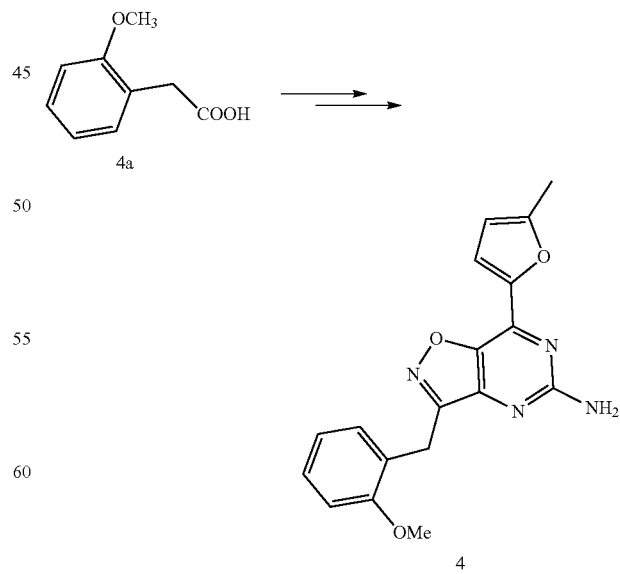

With reference to the preparation method of compound 1, compound 4 may be prepared from compound 4a by the corresponding steps, and the spectral information was as follows: $^1$H NMR (500 MHz, DMSO-d6) δ 7.43 (d, J=3.3 Hz, 1H), 7.28-7.22 (m, 1H), 7.14 (d, J=7.5 Hz, 1H), 7.02 (d, J=8.2 Hz, 1H), 6.88 (s, 2H), 6.88-6.79 (m, 1H), 6.50 (d, J=3.3 Hz, 1H), 4.18 (s, 2H), 3.79 (s, 3H), 2.45 (s, 3H); MS: 337.5 [M+H]$^+$.

Example 5

With reference to the preparation method of compound 1, compound 5 may be prepared from compound 5a by the corresponding steps, and the spectral information was as follows: $^1$H NMR (500 MHz, DMSO-d6) δ 7.44 (d, J=3.5 Hz, 1H), 7.40-7.35 (m, 4H), 6.90 (s, 2H), 6.50 (d, J=3.5 Hz, 1H), 4.28 (s, 2H), 2.45 (s, 3H); MS: 341.5 [M+H]$^+$.

Example 6

With reference to the preparation method of compound 1, compound 6 may be prepared from compound 6a by the corresponding steps, and the spectral information was as follows: $^1$H NMR (500 MHz, DMSO-d6) δ 7.45-7.24 (m, 5H), 6.91 (s, 2H), 6.51 (d, J=3.0 Hz, 1H), 4.30 (s, 2H), 2.45 (s, 3H); MS: 341.4 [M+H]$^+$.

Example 7

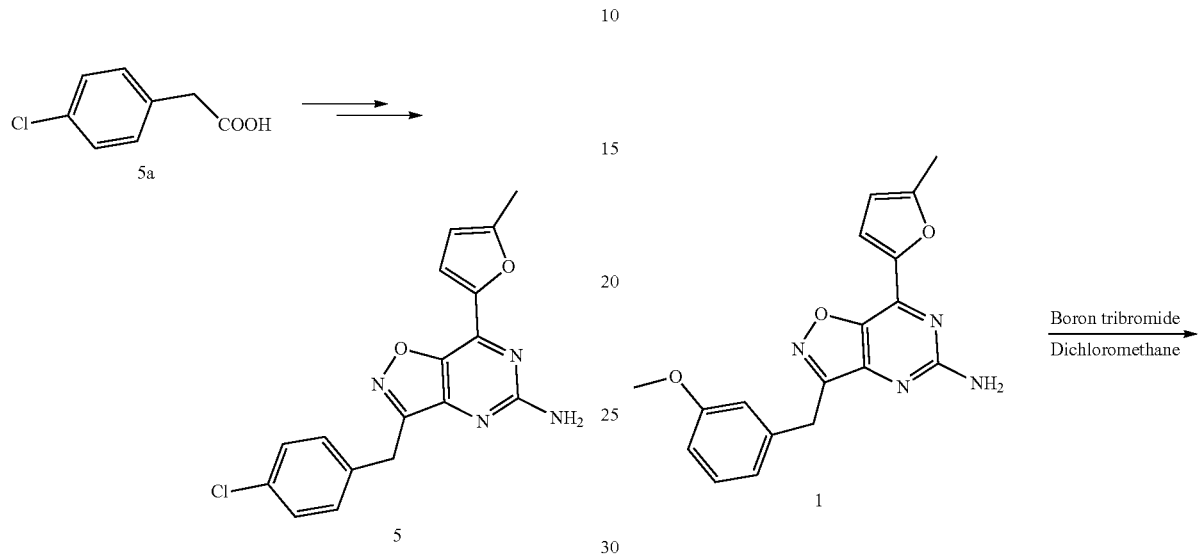

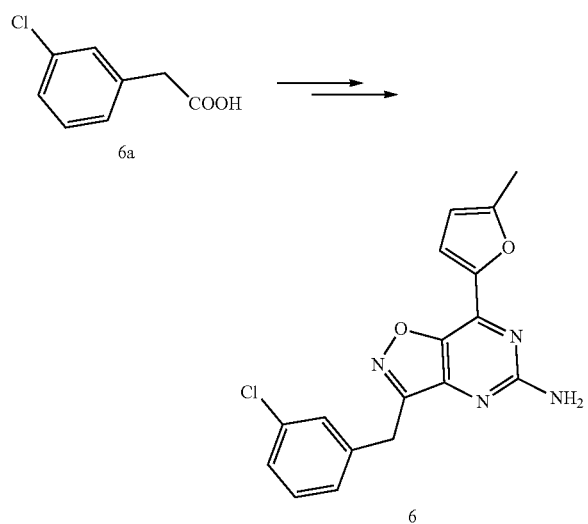

Boron tribromide (160 mg, 639 μmol) was added dropwise to a solution of compound 1 (43 mg, 128 μmol) in dichloromethane (5 mL) at −5° C., and the resulting solution was heated to room temperature for 1 hour. The reaction was quenched with water (20 mL) and then extracted with dichloromethane (20 mL×2). The combined organic layer was washed with saturated saline solution (20 mL), dried over anhydrous sodium sulfate, and filtered, and the filtrate was concentrated under reduced pressure to give a crude product, which was washed with a mixture solvent of ethyl acetate/methanol=20/1 (15 mL) to give the compound 7 as a yellow solid (12 mg, yield: 29%). $^1$H NMR (500 MHz, Methanol-d4) δ 7.51 (s, 1H), 7.10 (t, J=7.5 Hz, 1H), 6.83 (d, J=7.5 Hz, 1H), 6.80 (s, 1H), 6.64 (d, J=7.5 Hz, 1H), 6.41 (s, 1H), 4.21 (s, 2H), 2.47 (s, 3H); MS: 323.4 [M+H]$^+$.

Example 8

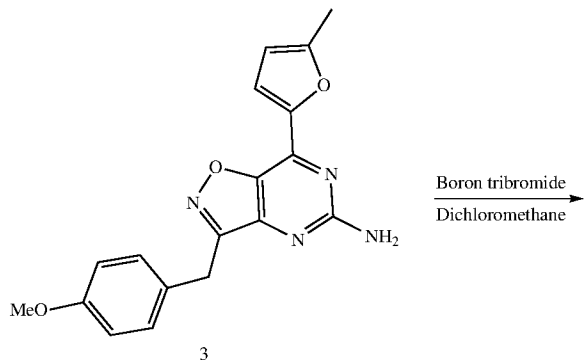

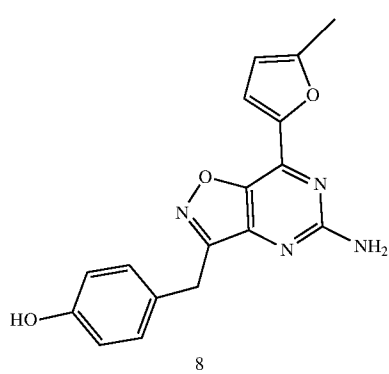

With reference to the preparation method of compound 7, compound 8 may be prepared from compound 3 by the corresponding steps, and the spectral information was as follows: $^1$H NMR (500 MHz, DMSO-d6) δ 9.32 (brs, 1H), 7.43 (d, J=3.0 Hz, 1H), 7.14 (d, J=8.5 Hz, 2H), 6.88 (brs, 2H), 6.69 (d, J=8.5 Hz, 2H), 6.50 (d, J=3.0 Hz, 1H), 4.13 (s, 2H), 2.45 (s, 3H); MS: 323.4 [M+H]$^+$.

Example 9

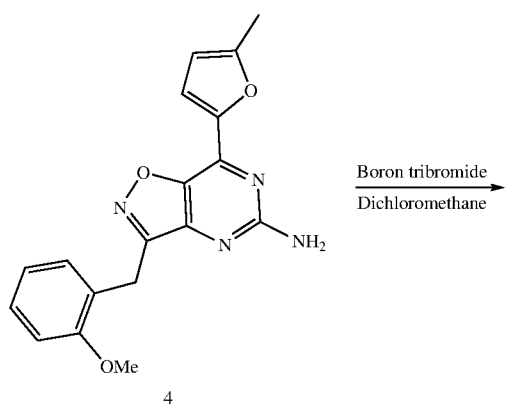

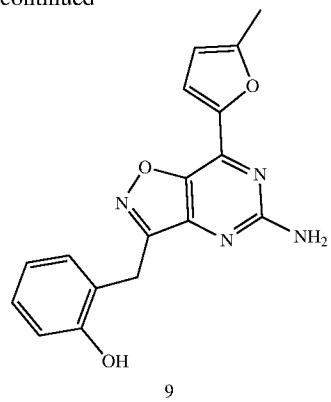

With reference to the preparation method of compound 7, compound 9 may be prepared from compound 4 by the corresponding steps, and the spectral information was as follows: $^1$H NMR (500 MHz, DMSO-d6) δ 9.58 (brs, 1H), 7.43 (d, J=3.0 Hz, 1H), 7.10-7.02 (m, 2H), 6.89 (brs, 2H), 6.85-6.81 (m, 1H), 6.74-6.69 (m, 1H), 6.50 (d, J=3.0 Hz, 1H), 4.15 (s, 2H), 2.45 (s, 3H); MS: 323.5 [M+H]$^+$.

Test Example

A2a/A2B Receptor Antagonist Functional Assay Test

The A2A cell line was derived from PerkinElmer (Product ID: ES-011-C); the A2B cell line was derived from PerkinElmer (Product ID: ES-013-C). The experimental procedure was referred to ACS Medicinal Chemistry Letters (2011) 2, 213-218; the specific test was completed by Pharmaron Beijing Co., Ltd. with the following steps: 10 nL of compound stock in DMSO (10 mM) followed by 10 µL of A2A or A2B cell suspension (30000 cells/mL) were transferred to assay wells of a 384-well plate at room temperature and incubated for 20 minutes at room temperature. The corresponding amount of 5'-N-ethylcarboxamido-adenosine at $EC_{80}$ activation concentration was transferred to each test well, and incubated for another 30 minutes at 37° C., 5% $CO_2$, 95% humidity, then Eu-cAMP tracer working solution and Ulight-anti-cAMP working solution were added to the cell culture plate at 5 uL/well in sequence, and the cell plate fluorescence was read with Envision (excitation wavelength: 320 nm, emission wavelength: 665 nm and 615 nm). The corresponding inhibition rate in each well was obtained according to the following formula, and a sigmoidal dose-inhibition rate curve was plotted using a non-linear regression model to calculate the $IC_{50}$ value.

$$\% \text{ Inhibition} = \left(1 - \frac{Ratio_{665mm/615mmhigh} - Ratio_{665mm/615mmcmpd}}{Ratio_{665mm/615mmhigh} - Ratio_{665mm/615mmlow}}\right) \times 100\%$$

The results of the binding affinity and antagonistic functional activity of the compounds listed in the examples for the A2A/A2B receptor are as follows:

| Compound Number | A2A Antagonistic function $IC_{50}$ (nM) | A2B Antagonistic function $IC_{50}$ (nM) |
| --- | --- | --- |
| 1 | 3.8 | 149 |
| 2 | 7.0 | |
| 3 | 120 | |

-continued

| Compound Number | A2A Antagonistic function IC$_{50}$ (nM) | A2B Antagonistic function IC$_{50}$ (nM) |
|---|---|---|
| 4 | 6.9 | |
| 5 | 31.8 | |
| 6 | 3.7 | |
| 7 | 11.0 | 11.0 |
| 8 | 80 | |
| 9 | 10.2 | |

The invention claimed is:

1. A compound of Formula (III) or a pharmaceutically acceptable salt, an isotopic derivative, an isomer, or a solvate thereof:

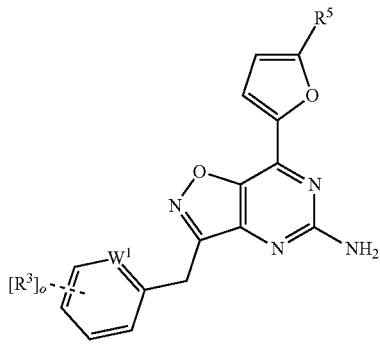

Formula (III)

wherein:

o is 1, 2 or 3;

$R^3$ is selected from $C_1$-$C_6$ alkyl, hydroxy ($C_1$-$C_6$ alkyl), $C_2$-$C_6$ alkenyl, $C_2$-$C_6$ alkynyl, $C_3$-$C_6$ cycloalkyl, $C_6$-$C_{12}$ aryl, 5-12 membered heteroaryl, $C_1$-$C_6$ haloalkyl, halogen, oxo, nitro, cyano, —NR$^a$R$^b$, —OR$^a$, —SR$^a$, —SOR$^a$, —SO$_2$R$^a$, —SO$_3$R$^a$, —NR$^a$C(O)R$^a$, —NR$^a$C(O)OR$^a$, —NR$^a$SO$_2$R$^a$, —C(O)OR$^a$, —C(O)NR$^a$R$^b$, —C(O)R$^a$, —(CR$^a$R$^b$)$_m$—OR$^a$, —(CR$^a$R$^b$)$_m$—NR$^a$R$^b$, —(CR$^a$R$^b$)$_m$—NR$^a$ —(CR$^a$R$^b$)$_n$—OR$^a$, —(CR$^a$R$^b$)$_m$—O—(CR$^a$R$^b$), —NR$^a$R$^b$, —(CR$^a$R$^b$)$_m$—O—(CR$^a$R$^b$), —OR$^a$ and —(CR$^a$R$^b$)$_m$—NR$^a$—(CR$^a$R$^b$)$_n$—NR$^a$R$^b$, or when o is 2 and the two $R^3$ substituents are located in adjacent positions, the two $R^3$ substituents are optionally cyclized with each other to form a saturated or unsaturated 4-7 membered ring comprising 0, 1, or 2 heteroatoms selected from O, S, and N;

$R^a$ and $R^b$ are independently selected from hydrogen, halogen, $C_1$-$C_6$ alkyl, $C_3$-$C_6$ cycloalkyl and —($C_0$-$C_6$ alkylene)-($C_6$-$C_{12}$) aryl, or when $R^a$ and $R^b$ are attached to the same atom, $R^a$ and $R^b$ together with the atom to which they are attached are optionally cyclized to form a saturated or unsaturated 4-7 membered ring comprising 0, 1, or 2 heteroatoms selected from O, S, and N;

m is 0, 1, 2, 3 or 4;

n is 0, 1, 2, 3 or 4;

$W^1$ is selected from CR$^4$ and N;

$R^4$ is selected from $C_1$-$C_6$ alkyl, hydroxy ($C_1$-$C_6$ alkyl), $C_2$-$C_6$ alkenyl, $C_2$-$C_6$ alkynyl, $C_3$-$C_6$ cycloalkyl, $C_6$-$C_{12}$ aryl, 5-12 membered heteroaryl, $C_1$-$C_6$ haloalkyl, halogen, oxo, nitro, cyano, —NR$^a$R$^b$, —OR$^a$, —SR$^a$, —SOR$^a$, —SO$_2$R$^a$, —SO$_3$R$^a$, —NR$^a$C(O)R$^a$, —NR$^a$C(O)OR$^a$, —NR$^a$SO$_2$R$^a$, —C(O)OR$^a$, —C(O)NR$^a$R$^b$, —C(O)R$^a$, —(CR$^a$R$^b$)$_m$—OR$^a$, —(CR$^a$R$^b$)$_m$—NR$^a$R$^b$, —(CR$^a$R$^b$)$_m$—NR$^a$ —(CR$^a$R$^b$)$_n$—OR$^a$, —(CR$^a$R$^b$)$_m$—O—(CR$^a$R$^b$), —NR$^a$R$^b$, —(CR$^a$R$^b$)$_m$—O—(CR$^a$R$^b$)$_n$—OR$^a$ and —(CR$^a$R$^b$)$_m$—NR$^a$—(CR$^a$R$^b$)$_n$—NR$^a$R$^b$;

$R^5$ is selected from hydrogen, $C_1$-$C_6$ alkyl, $C_2$-$C_6$ alkenyl, $C_2$-$C_6$ alkynyl, $C_3$-$C_6$ cycloalkyl, $C_1$-$C_6$ haloalkyl, $C_1$-$C_6$ alkoxy, $C_1$-$C_6$ alkylthio, halogen, nitro, —NR$^c$R$^d$, cyano, —SO$_2$R$^c$, and —SO$_3$R$^c$; and $R^c$ and $R^d$ are independently selected from hydrogen, halogen, $C_1$-$C_6$ alkyl and $C_3$-$C_6$ cycloalkyl, or when $R^c$ and $R^d$ are attached to the same atom, $R^c$ and $R^d$ together with the atom to which they are attached are optionally cyclized to form a saturated or unsaturated 3-7 membered ring comprising 0, 1, or 2 heteroatoms selected from O, S, and N.

2. The compound according to claim 1, which is selected from:

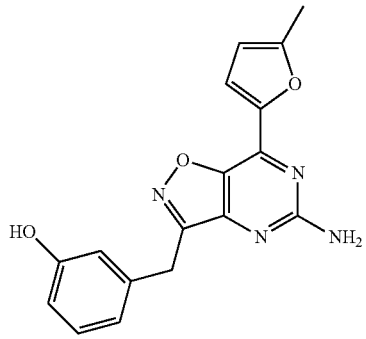

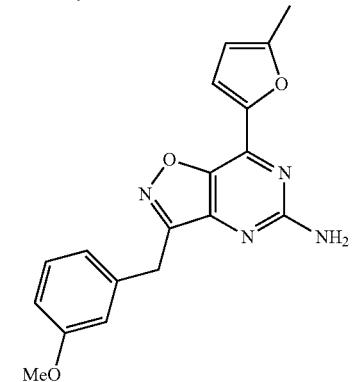

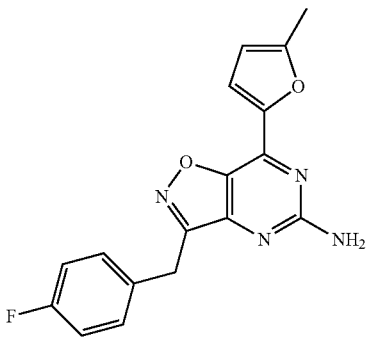

-continued

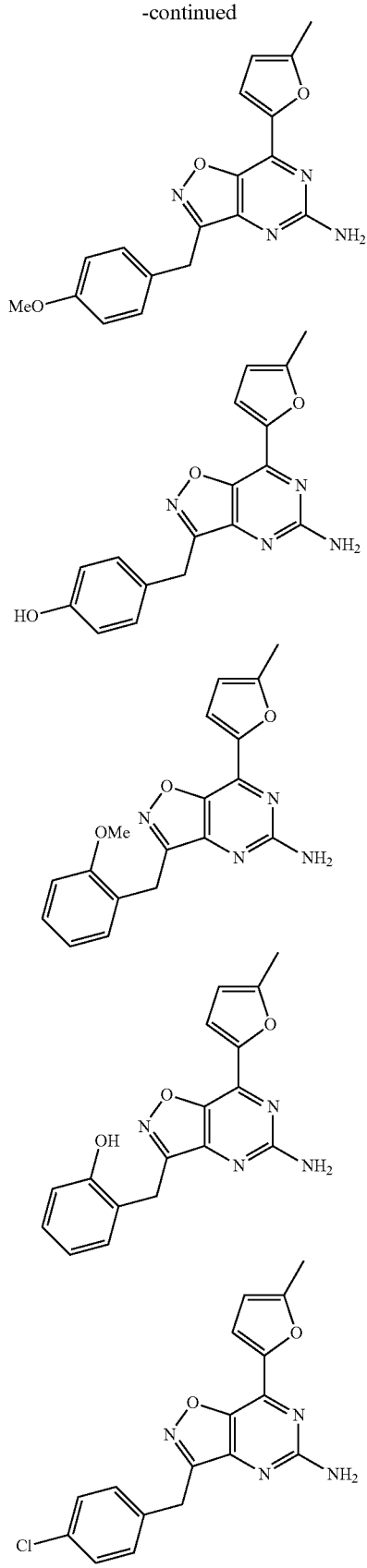

-continued

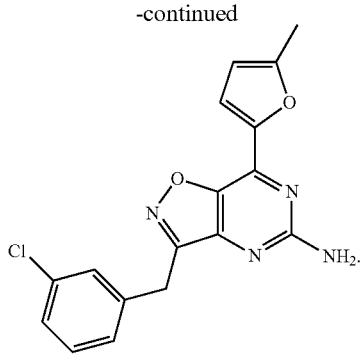

3. A pharmaceutical composition comprising the compound of Formula (III) or a pharmaceutically acceptable salt, an isotopic derivative, an isomer, or a solvate thereof according to claim 1, and optionally a pharmaceutically acceptable carrier.

4. The pharmaceutical composition according to claim 1, further comprising an additional therapeutic agent and/or a checkpoint inhibitor, wherein the additional therapeutic agent is selected from Chlorambucil, Melphalan, Cyclophosphamide, Ifosfamide, Busulfan, Carmustine, Lomustine, Streptozotocin, Cisplatin, Carboplatin, Oxaliplatin, Dacarbazine, Temozolomide, Procarbazine, Methotrexate, Fluorouracil, Cytarabine, Gemcitabine, Mercaptopurine, Fludarabine, Vinblastine, Vincristine, Vinorelbine, Paclitaxel, Docetaxel, Topotecan, Irinotecan, Etoposide, Trabectedin, Dactinomycin, Doxorubicin, Epirubicin, Daunorubicin, Mitoxantrone, Bleomycin, Mitomycin C, Ixabepilone, Tamoxifen, Flutamide, Gonadorelin Analogs, Megestrol, Prednisone, Dexamethasone, Methylprednisolone, Thalidomide, Interferon α, Calcium Folinate, Sirolimus, Temsirolimus, Everolimus, Afatinib, Alisertib, Amuvatinib, Apatinib, Axitinib, Bortezomib, Bosutinib, Brivanib, Cabozantinib, Cediranib, Crenolanib, Crizotinib, Dabrafenib, Dacomitinib, Danusertib, Dasatinib, Dovitinib, Erlotinib, Foretinib, Ganetespib, Gefitinib, Ibrutinib, Icotinib, Imatinib, Iniparib, Lapatinib, Lenvatinib, Linifanib, Linsitinib, Masitinib, Momelotinib, Motesanib, Neratinib, Nilotinib, Niraparib, Oprozomib, Olaparib, Pazopanib, Pictiliisib, Ponatinib, Quizartinib, Regorafenib, Rigosertib, Rucaparib, Ruxolitinib, Saracatinib, Saridegib, Sorafenib, Sunitinib, Telatinib, Tivantinib, Tivozanib, Tofacitinib, Trametinib, Vandetanib, Veliparib, Vemurafenib, Vismodegib, Volasertib, Alemtuzumab, Bevacizumab, Brentuximab Vedotin, Catumaxomab, Cetuximab, Denosumab, Gemtuzumab, Ipilimumab, Nimotuzumab, Ofatumumab, Panitumumab, Rituximab, Tositumomab, and Trastuzumab; the checkpoint inhibitor is preferably selected from anti-PD-1 antibodies, anti-PD-L1 antibodies, LAG3 antibodies, TIM-3 antibodies, and anti-CTLA-4 antibodies.

* * * * *

UNITED STATES PATENT AND TRADEMARK OFFICE
CERTIFICATE OF CORRECTION

PATENT NO. : 12,410,188 B2  
APPLICATION NO. : 17/630846  
DATED : September 9, 2025  
INVENTOR(S) : Yu et al.

Page 1 of 1

It is certified that error appears in the above-identified patent and that said Letters Patent is hereby corrected as shown below:

In the Claims

Claim 1, Column 29, Lines 45-46, please delete "-$(CR^aR^b)_m$-O-$(CR^aR^b)$,-$NR^aR^b$, -$(CR^aR^b)_m$-O-$(CR^aR^b)$,-$OR^a$" and insert -- -$(CR^aR^b)_m$-O-$(CR^aR^b)_n$-$NR^aR^b$, -$(CR^aR^b)_m$-O-$(CR^aR^b)_n$-$OR^a$ -- therefor.

Claim 1, Column 30, Lines 5-6, please delete "-$(CR^aR^b)_m$-O-$(CR^aR^b)$,-$NR^aR^b$," and insert -- -$(CR^aR^b)_m$-O-$(CR^aR^b)_n$-$NR^aR^b$, -- therefor.

Claim 4, Column 32, Line 61, please delete "inhibitor is preferably selected from" and insert -- inhibitor is selected from -- therefor.

Signed and Sealed this  
Sixth Day of January, 2026

John A. Squires  
*Director of the United States Patent and Trademark Office*